United States Patent
De Haan et al.

(10) Patent No.: US 11,136,602 B2
(45) Date of Patent: Oct. 5, 2021

(54) FERMENTATION PROCESS

(71) Applicant: PURAC BIOCHEM BV, Gorinchem (NL)

(72) Inventors: Andre Banier De Haan, Gorinchem (NL); Jeroen Bokhove, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 272 days.

(21) Appl. No.: 16/462,978

(22) PCT Filed: Nov. 29, 2017

(86) PCT No.: PCT/EP2017/080790
§ 371 (c)(1),
(2) Date: May 22, 2019

(87) PCT Pub. No.: WO2018/099954
PCT Pub. Date: Jun. 7, 2018

(65) Prior Publication Data
US 2019/0309332 A1   Oct. 10, 2019

(30) Foreign Application Priority Data

Nov. 29, 2016 (EP) .................................... 16201215

(51) Int. Cl.
| | |
|---|---|
| *C12P 7/56* | (2006.01) |
| *C12M 1/34* | (2006.01) |
| *C12M 1/00* | (2006.01) |
| *C12P 7/40* | (2006.01) |
| *C12P 7/46* | (2006.01) |
| *C12P 7/48* | (2006.01) |
| *C12P 7/52* | (2006.01) |
| *C12P 7/58* | (2006.01) |

(52) U.S. Cl.
CPC .............. *C12P 7/56* (2013.01); *C12M 41/40* (2013.01); *C12M 41/44* (2013.01); *C12M 47/12* (2013.01); *C12P 7/40* (2013.01); *C12P 7/46* (2013.01); *C12P 7/48* (2013.01); *C12P 7/52* (2013.01); *C12P 7/58* (2013.01)

(58) Field of Classification Search
CPC ..... C12P 7/56; C12P 7/40–60; B01B 1/00–02
See application file for complete search history.

(56) References Cited

U.S. PATENT DOCUMENTS

| | | | |
|---|---|---|---|
| 4,349,628 A | 9/1982 | English et al. | |
| 4,460,687 A | 7/1984 | Ehnstrom | |
| 6,077,549 A | 6/2000 | Bodmer et al. | |
| 6,509,179 B1 * | 1/2003 | Veldhuis-Stribos | .... C07C 51/02 435/139 |
| 2012/0220003 A1 | 8/2012 | Schwartz et al. | |
| 2012/0244587 A1 | 9/2012 | Van Breugel et al. | |
| 2016/0207868 A1 | 7/2016 | Kawamura et al. | |

FOREIGN PATENT DOCUMENTS

| | | | | |
|---|---|---|---|---|
| EP | 2311968 A1 * | 4/2011 | ................ | C12P 7/46 |
| JP | S46-41583 B2 | 12/1971 | | |
| JP | S59-39293 A | 3/1984 | | |
| JP | 2003-310243 A | 11/2003 | | |
| JP | 2008-259517 A | 10/2008 | | |
| JP | 2010-193846 A | 9/2010 | | |
| WO | WO-9300440 A1 * | 1/1993 | ............. | C07C 67/08 |
| WO | WO-9413826 A1 * | 6/1994 | ............. | C12P 19/14 |
| WO | WO-9919290 A2 * | 4/1999 | ............. | C07C 51/48 |
| WO | 2015/034036 A1 | 3/2015 | | |

OTHER PUBLICATIONS

Feb. 11, 2020 Office Action issued in Russian Patent Application No. 2019117574/10.
Feb. 11, 2020 Search Report issued in Russian Patent Application No. 2019117574/10.
Jul. 9, 2020 Office Action issued in Japanese Patent Application No. 2019-527898.
Apr. 19, 2018 International Search Report issued in International Patent Application No. PCT/EP2017/080790.
Apr. 19, 2018 Written Opinion issued in International Patent Application No. PCT/EP2017/080790.
Jun. 2, 2021 Office Action issued in Japanese Patent Application No. 2019-527898.

* cited by examiner

*Primary Examiner* — Thane Underdahl
(74) *Attorney, Agent, or Firm* — Oliff PLC

(57) ABSTRACT

A fermentation product manufacturing process includes fermenting under fermentation conditions in an aqueous fermentation medium in a fermentation reactor a carbohydrate source with a microorganism capable of converting the carbohydrate into a fermentation product which is a salt or a product with a boiling point above the boiling point of water, during the process withdrawing part of the medium including biomass from the reactor in the form of a recycle stream, providing the stream including biomass to a pressure vessel wherein the pressure is such that the temperature of the stream decreases 1-8° C., as compared to the temperature of the medium in the reactor, by the evaporation of water, and recycling the cooled recycle stream to the reactor. The process makes it possible to obtain a homogeneous temperature profile of the fermentation medium with limited occurrence of hot or cool spots within the reactor which results in improved fermentation performance.

15 Claims, 1 Drawing Sheet

FERMENTATION PROCESS

The present invention pertains to a fermentation process comprising fermenting a carbohydrate source under fermentation conditions with a microorganism.

Fermentation processes wherein a carbohydrate source is fermented under fermentation conditions with a microorganism capable of converting the carbohydrate into a fermentation product are known in the art, and are applied to manufacture a variety of fermentation products.

It has been found that problems may occur during fermentation processes on industrial scale, especially where large reactor volumes, relatively high fermentation temperatures, and high biomass and fermentation product concentrations are at issue. This is because in these situations it has been found that it is difficult to keep the temperature in the reaction vessel constant over the entire volume of the reaction vessel. This is important for various reasons.

On the one hand, at locations in the reactor vessel where the temperature is relatively low, crystallisation of the fermentation product may occur if the fermentation product has a limited solubility in water. This may result in scale formation on cool surfaces, such as the surface of heat exchangers, which are often employed in fermentation vessels. This scale formation detrimentally affects the functioning of the heat exchanger. Additionally, crystallization of the fermentation product on cool surfaces also leads to formation of crystals with inhomogeneous structure, which is undesirable.

Further, cool spots in the fermentation unit can affect the production capacity of microorganisms at that location of the reactor. Microorganisms generally have an optimum production temperature, and when they are at a temperature below that value, their activity will decrease, which is of course undesirable.

Conversely, at locations in the fermentation unit where the temperature is relatively high, undesirable effects may also be obtained. In particular, temperatures which are too high may again lead to a decreased activity of the microorganism. Further, high temperatures may result in the formation of undesirable side products.

In the art, temperature control fermentation processes where large reactor volumes, relatively high fermentation temperatures, and high biomass and fermentation product concentrations are at issue has often been carried out by providing heat exchangers in the reactor in combination with homogenizing elements such as stirrers. However, it has been found that these elements are not always adequate. As described above, scaling of fermentation product with limited solubility on the heat exchangers is a problem as is the formation of cool spots. A further problem is that the addition of heat exchangers detracts from the free reactor volume, and if extensive cooling is required, they may not be sufficient space in the reactor to be able to fit in the required cooling capacity. Additionally, heat exchangers are expensive, and relatively inflexible in that once present they can only be removed when the reactor has been shut down.

There is need in the art for a fermentation process which ensures a constant reaction temperature over the entire unit, also where large reactor volumes, relatively high fermentation temperatures, and high biomass and fermentation product concentrations are at issue. There is further need for a fermentation process where a homogeneous reaction temperature can be obtained with limited financial investment, and wherein the temperature control is flexible in that the cooling action can be directly adapted to the needs of the process. The present invention provides a process which solves these problems.

The invention pertains to a fermentation process comprising fermenting under fermentation conditions in an aqueous fermentation medium in a fermentation reactor a carbohydrate source with a microorganism capable of converting the carbohydrate into a fermentation product, during the fermentation process withdrawing part of the fermentation medium comprising biomass from the fermentation reactor in the form of a recycle stream, providing the recycle stream comprising biomass to a pressure vessel wherein the pressure is selected such that the temperature of the recycle stream decreases with a value of 1-8° C., as compared to the temperature of the fermentation medium in the fermentation reactor, by the evaporation of water, recycling the cooled recycle stream to the fermentation reactor.

It has been found that the process according to the invention makes it possible to obtain a homogeneous temperature profile of the fermentation medium with limited occurrence of hot or cool spots within the reactor. This has been found to result in improved fermentation performance.

A key feature of the process according to the invention is the withdrawal of part of the fermentation medium, and providing it to a pressure vessel, where it is cooled down to a specified degree with evaporation of water, and recycling the cooled stream to the fermentation reactor.

It is noted that US2012/0220003 describes a method for continuous separation of organic materials of interest from a fermentation, in particular a lactic or alcoholic fermentation wherein fermentation medium is withdrawn from the fermentor and provided to a flash evaporator, where volatile fermentation products are flashed from the fermentation medium. It is indicated that biomass is separated from the fermentation medium before it is provided to the flash evaporator. This is in contrast with the present invention where biomass is not removed from the recycle stream. It is a feature of the present invention that due to the relative mildness of the pressure reduction step, as can be seen from the limited temperature reduction, removal of biomass before the pressure reduction step is not required. This results in substantial savings, not only in acquisition costs for the apparatus required for the biomass separation step, but also for the maintenance of the apparatus. Further, the biomass separation step as carried out in this reference in itself detrimental to the properties of the biomass.

JP59039293 describes an alcohol fermentation wherein part of the fermentation medium is withdrawn from the fermentation reactor, subjected to flash evaporation, and returned to the fermentation reactor. In this reference, the biomass is immobilized on a carrier. Where biomass is immobilized on a carrier, the temperature in the fermentation reactor will always be inhomogeneous.

US2012/0244587 describes performing a fermentation under reduced pressure with water being evaporated and removed from the reactor during the fermentation in an amount which is at least 20% of the volume of liquid present in the reactor at the start of the fermentation. This reference does not describe withdrawing part of the fermentation medium from the fermentation reactor, providing this stream to a pressure vessel wherein the pressure is selected such that the temperature of the recycle stream decreases with a value of 1-8° C. as compared to the temperature of the fermentation medium in the fermentation reactor, and recycling the stream to the fermentation reactor.

U.S. Pat. No. 4,349,628 describes a fermentation process for the manufacture of volatile organic components wherein continuously a portion of the fermentation medium is provided to a separator where ethanol or other volatile components are evaporated at a temperature which is not deleterious to the microorganism by subjecting the fermentation medium to a reduced pressure and recycling part or all of the remaining fraction to the fermenter. The purpose of this process is to remove volatile components from the system as they can be toxic for the microorganism. It is indicated that the material to be recycled to the reactor should have a temperature which is as high as possible, as long as it does not affect the survival of the microorganism. This is different from the presently claimed invention which uses water evaporation from a fermentation of a product with a boiling point above that of water to effect temperature control.

The invention will be discussed in more detail below.

The invention will be illustrated with reference to the following figures, without being limited thereto or thereby.

Figure 1:
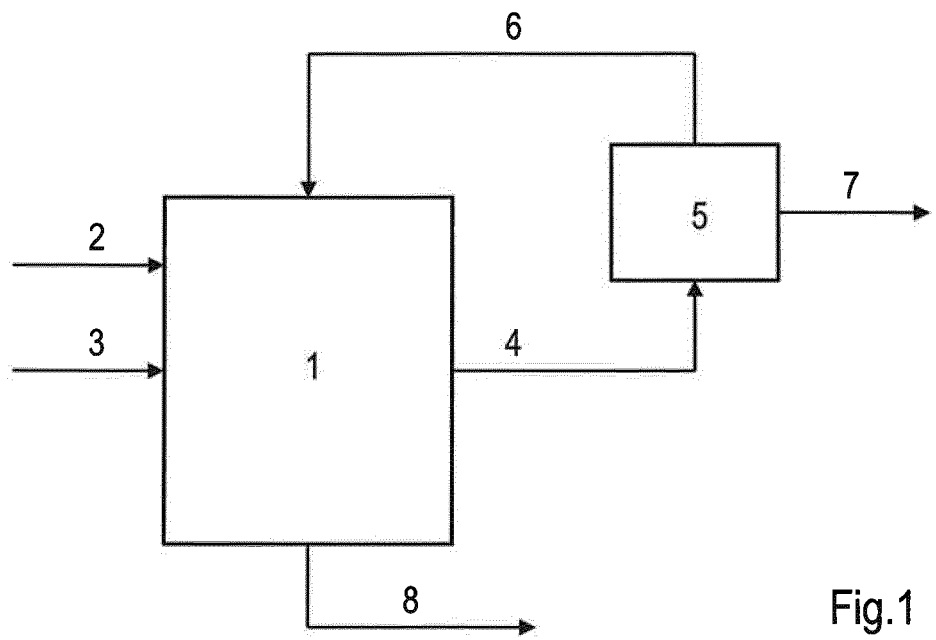
FIG. 1 illustrates a first embodiment of the present invention.

In FIG. 1, a fermentation process is carried out in fermentation reactor (1). Nutrients and carbohydrate source can be provided through line (2). A neutralising compound can be provided through line (3). Obviously, these lines can be combined, or nutrients and carbohydrate can be provided through separate lines. It is also possible for all these compounds to be added to the reactor at the beginning of the reaction, in which case these lines can be dispensed with. During the fermentation process part of the fermentation medium comprising biomass is withdrawn from the fermentation reactor through line (4), and provided to the pressure vessel (5). In the pressure vessel water is evaporated and withdrawn through line (7). The resulting cooled recycle stream is recycled back to the fermentation reactor through line (6). Fermentation medium can be withdrawn from the reactor through line (8). This can be done continuously, intermittently, or once the fermentation has been completed, depending on the process configuration.

The first step in the process according to the invention is fermenting a carbohydrate source under fermentation conditions in an aqueous fermentation medium in a fermentation reactor with a microorganism capable of converting the carbohydrate into a fermentation product, wherein the fermentation product is a salt or a product with a boiling point above the boiling point of water. The nature of the fermentation product is not critical to the process according to the invention.

In one embodiment the present invention pertains to a fermentation process to manufacture a product comprising a salt of an acid. In these fermentation processes, the microorganism produces an acid, and base is added to the fermentation medium to keep the pH within the range required for the microorganism at issue, converting the acid in whole or in part to its corresponding salt.

Acids that may be manufactured via the process according to the invention include carboxylic acids, in particular carboxylic acids selected from the group consisting of mono-, di-, and tricarboxylic acids having 2-8 carbon atoms. Examples include lactic acid, propionic acid, citric acid, malic acid, maleic acid, fumaric acid, adipic acid, succinic acid, tartaric acid, alpha-ketoglutaric acid, oxaloacetic acid, acetic acid, acrylic acid, furan-dicarboxylic acid (FDCA), gluconic acid, glycolic acid, malonic acid, 3-hydroxy propionic acid, butyric acid, 3-hydroxy butyric acid, valeric acid, isovaleric acid, caproic acid and/or salts thereof. The invention may be particularly attractive where the fermentation product has a low solubity in water, e.g., the case of low-solubility acids or salts. The invention has been found to be particularly attractive for magnesium and calcium lactate fermentations, in particular magnesium lactate. The invention may also be particularly attractive for magnesium FDCA and magnesium succinate.

As discussed above, during the fermentation, the formation of acid results in a decrease in the pH. To counter this and keep the pH within the range where the microorganism can perform, a basic solution is typically added during the fermentation. Suitable basic solutions contain solutions comprising one or more of calcium (hydr)oxide, calcium carbonate, calcium bicarbonate, magnesium (hydr)oxide, sodium hydroxide, ammonium hydroxide, potassium hydroxide, magnesium carbonate, sodium bicarbonate, potassium bicarbonate. Depending on the solubility of the base, the basic solution mentioned above may be a true solution in the sense that the base is completely dissolved and the solution does not contain solid components. However, the basic solution may also be a slurry, which contains solid particles in addition to dissolved base. Within the present specification the word solution is intended to encompass both embodiments.

Generally, the basic solution is added in an amount effective to control the pH of the broth between about 3 and 9, more specifically between 5.5 and about 7.0.

The nature of the hydrocarbon source is not critical to the present invention. The carbohydrate source generally comprises one or more of sugars, (liquefied) starch, sugar syrup, or cheese whey, glucose, fructose, or galactose, or disaccharides such as sucrose or lactose, hexoses and pentoses in hydrolysates of plant origin, such as biowaste, wood, straw, etc.

It is well within the scope of the skilled person to select a microorganism and fermentation conditions which will result in obtaining the desired fermentation product. This requires no further elucidation here. The process according to the invention has been found to be particularly attractive for processes which use a microorganism which has a temperature optimum which is relatively high, as these organisms may be particularly sensitive to cool spots in the unit. Further, fermentation processes carried out at higher temperatures may be particularly sensitive to temperature runaway, requiring controlled cooling. Therefore, in one embodiment, the temperature in the fermentation reactor is in the range of 30-65° C., in particular in the range of 40-60° C. The heat in the reaction medium has various causes. It is generated in part by the microorganism itself, but also by equipment such as stirrers and pumps. It is also added with the neutralization agent and the feed compounds. The present invention allows proper management of reactor temperature.

The process of the present invention may be particularly attractive for situations where the concentration of fermentation product present in the fermentation medium is close to, at, or above the saturation concentration. In this case, the method according to the invention prevents the presence of "cool spots" in the reactor, which could lead to uncontrolled precipitation of solid fermentation product. This could lead to scaling on the heat exchangers, and/or the formation of precipitated (crystals of) solid fermentation product with inhomogeneous particle size or crystal properties. In one embodiment, the concentration of fermentation product in the fermentation medium is above 70% of the saturation concentration, in particular above 80%, in some embodiments above 90%, during at least part of the operating time of the fermentation process.

The invention may be particularly attractive when the fermentation medium contains solid fermentation product during at least part of the operating time of the fermentation process, as fermentations of this type are particularly sensitive to uncontrolled crystallization, e.g., on cool spots in the reactor. In one embodiment, during at least 20% of the operating time of the fermentation process, the fermentation medium contains solid fermentation product in an amount of at least 1 vol. %, calculated as solid fermentation product on the total of the fermentation medium.

Here, the starting point for the operating time of the fermentation process is the point in time when all medium components have been provided to the reactor, the fermentation medium has been brought to fermentation conditions, such as the selected pH and temperature, and the microorganism has been provided to the reactor. At that point in time all conditions have been met for the fermentation to begin. The end point for the operating time of the fermentation process is the point in time when product formation has essentially stopped, i.e., when the production in g/l·h. is below 10% of the maximum value of production in g/l·h during the process. This will generally be when the carbon source has been depleted.

The percentage of operating time during which solid fermentation product is present in the fermentation medium will depend on the fermentation at issue, and may be much longer than 20%. Generally, where solid fermentation product is present during at least part of the operating time, it may be preferred for the solid fermentation product to be present during a relatively large part of the operating time. In this case the fermentation is a highly concentrated fermentation. The percentage of the operating time during which solid fermentation product is present may be at least 40%, in some embodiments at least 60%, sometimes at least 70%, in some specific embodiments least 80% and even at least 90%. The amount of solid fermentation product may vary within wide ranges. If present, it may be preferred for it to be present in an amount of at least 5%, in some embodiments at least 10%. As a general maximum, a value of 50% may be given, as it may be difficult to operate a fermentation at higher concentrations in view of processing issues. It may be preferred for the amount of solid fermentation product to be at most 40%, more in particular at most 35%.

The concentration of solid fermentation product in the fermentation medium can be determined in accordance with the following procedure: A 1 ml homogeneous sample is taken from the fermentation broth using an Eppendorf tube. The sample is centrifuged for 2 minutes at 1300 rpm. The volume percentage of the solid layer is determined visually.

This solid layer comprises both solid fermentation product and biomass. To compensate for the amount of biomass, the amount of biomass may be determined separately by methods known in the art, e.g., by determining the optical density at 600 nm of a fermentation broth sample from which crystals have been removed by diluting it to 5 vol. % in a solution of 0.5N EDTA adjusted to pH 8 with KOH, and comparing it with the OD600 nm of standard biomass solutions. The volume percentage of solid fermentation product can then be determined by subtracting the volume percentage of biomass from the percentage obtained in the centrifuge procedure described above.

The fermentation is carried out in a fermentation reactor. It has been found that the problems associated with inhomogeneous heating and cooling are particularly relevant for fermentations which are carried out in large reactor volumes. Therefore, in one embodiment, the size of the fermentation reactor is such that the volume of fermentation medium in the fermentation reactor is at least 100 m3. Fermentation reactors of larger size may also be used. The volume of fermentation medium in the fermentation reactor can for example be at least 200 m3, or even at least 400 m3. As a general maximum a value of 2000 m3 may be mentioned.

The fermentation reactor can be equipped with conventional reactor equipment like stirrers or other means for homogenising the fermentation medium. It may be preferred for the reactor not to contain heat exchangers. Heat exchangers may interfere with the mixing carried out to obtain a homogeneous medium, and it is a feature of the present invention that heat exchangers are not necessary.

During the fermentation process, part of the fermentation medium comprising biomass is withdrawn from the fermentation reactor in the form of a recycle stream. The recycle stream comprising biomass is provided to a pressure vessel wherein the pressure is selected such that the temperature of the recycle stream decreases with a value of 1-8° C., as compared to the temperature of the fermentation medium in the fermentation reactor by the evaporation of water. The cooled recycle stream is provided back to the fermentation reactor.

This recycle step through a pressure vessel is intended to cool the fermentation medium in the fermentation process in a homogeneous manner. The extent of cooling will depend on the temperature reduction in the pressure vessel and on the amount of fermentation medium which is recycled through the pressure vessel.

The pressure vessel is operated under such conditions that the temperature of the recycle stream decreases with a 1-8° C., as compared to the temperature of the fermentation medium. A decrease in temperature below 1° C. is too low to effect meaningful cooling. A decrease in temperature above 8° C. may lead to an inhomogeneous temperature profile in the fermentation reactor when the medium is recycled thereto.

To effect adequate temperature control of the fermentation medium in the fermentation reactor, it may be preferred if the temperature of the recycle stream decreases with a value of 2-5° C., as compared to the temperature of the fermentation medium in the fermentation reactor. The temperature reduction in the pressure vessel is obtained by evaporation of water. It is within the scope of the skilled person to select pressure conditions resulting in the desired temperature decrease.

It is noted that, as in the present invention the fermentation product is a salt or a product with a boiling point above the boiling point of water, no evaporation of fermentation product in the pressure vessel will occur. Evaporation of low boiling side products can take place if they are formed, but the purpose of the recycle through the pressure vessel is temperature reduction and not side product evaporation.

The volume of the pressure vessel generally is relatively small as compared to the volume of the fermentation reactor. Preferably it is between 0.1 and 10 percent of the volume of the fermentation reactor. If the volume of the pressure vessel is too small, it will be difficult to obtain adequate cooling. If the volume of the pressure vessel is too large, the cost of the apparatus will increase without substantial benefit to the process. The volume of the pressure vessel may for example be between 0.5 and 10 m3, in particular between 1 and 5 m3.

The recycle time is generally relatively short in the process according to the invention. A shorter recycle time is preferred because in the recycle section the microorganism is under less controlled conditions than in the reactor. More in particular, the recycle time, defined as the time between withdrawal of a fraction of fermentation medium from the fermentation reactor and reintroduction of the fraction into the reactor after cooling is at most 10 minutes, in particular at most 5 minutes. No benefit is expected from a longer recycle time. The minimum recycle time is dependent on the exact configuration of the apparatus, and not critical.

The recycle frequency can be adapted to obtain the required temperature control. It will depend, among others, on the size of the pressure vessel and the size of the fermentation reactor. In one embodiment the recycle frequency is selected such that per hour 0.1 to 10 times the volume of the fermentation reactor is recycled through the pressure vessel. It may be preferred to recycle 0.5 to 5 times the volume of the fermentation reactor through the pressure vessel per hour, more in particular. 0.5 to 2 times the volume of the fermentation reactor per hour.

The fermentation process may be a batch process, a fed-batch process, or a continuous process. The process according to the invention may be a batch process, a fed-batch process, or a continuous process.

In one embodiment, the fermentation process according to the invention is a batch process. Within the present specification a batch process is defined as a process wherein the carbon source is provided to the fermentation reactor at the beginning of the reaction, and no (substantial portions of) carbon source are provided during the process.

In one embodiment, the fermentation process according to the invention is a fed-batch process. Within the present specification a fed-batch process is a process wherein at least the carbon source is provided to the fermentation reactor at the beginning of the reaction and during the reaction, which process has a predetermined end point beyond which fermentation cannot be continued due to, e.g., the build-up of impurities.

In one embodiment, the fermentation process according to the invention is a continuous fermentation process. Within the context of the present specification a continuous fermentation process is a process wherein at least the carbon source is provided to the fermentation reactor at the beginning of the reaction and during the reaction, wherein the process does not have a predetermined end point. In general, the total volume of the fermentation medium is kept more or less constant. This means that, in view of the addition of carbon source during the fermentation which results in an increase in the volume of the fermentation medium, reactor content will be removed during the fermentation. This may be solid fermentation product and/or liquid fermentation medium. In principle, a continuous fermentation can run indefinitely, although it will at some point in time be discontinued for unit maintenance. The concepts of batch fermentation, fed-batch fermentation, and continuous fermentation are known to the skilled person.

In FIG. 1 the embodiment has been illustrated where the apparatus required for the cooling step is connected directly to the fermentation reactor. It is also possible to integrate the apparatus required for the cooling step into a step where fermentation product is removed.

Figure 2:
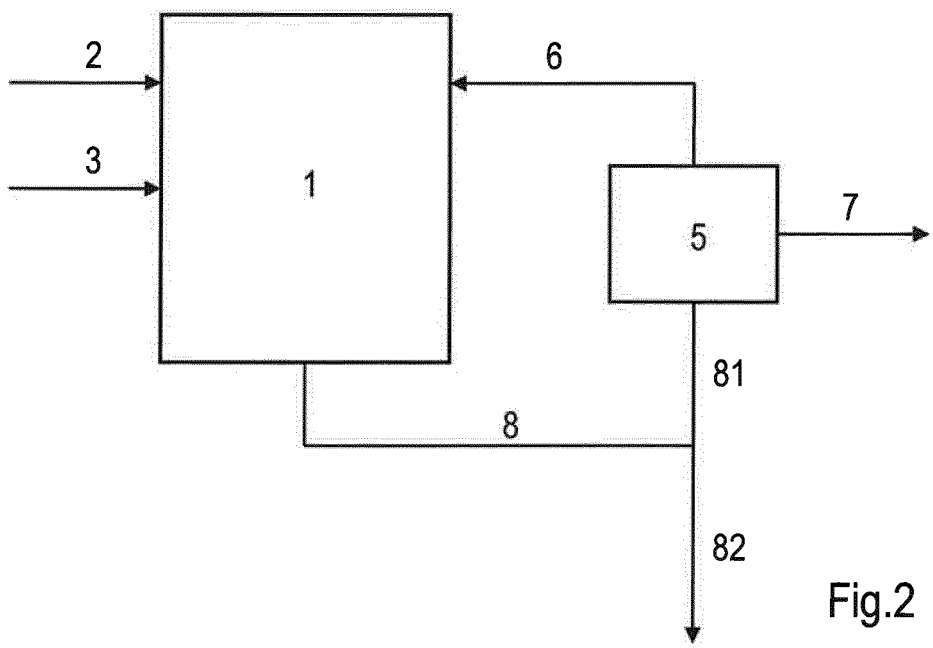
FIG. 2 illustrates a further embodiment of the present invention.

One embodiment of this process is illustrated in FIG. 2. In FIG. 2, a fermentation process is carried out in fermentation reactor (1). Nutrients and carbohydrate source can be provided through line (2). A neutralising compound can be provided through line (3). As for FIG. 1, these lines can be combined, or nutrients and carbohydrate can be provided through separate lines. It is also possible for all these compounds to be added to the reactor at the beginning of the reaction, in which case these lines can be dispensed with.

During the fermentation process part of the fermentation medium comprising biomass is withdrawn from the fermentation reactor through line (8). Line (8) divides into line (81) and line (82). Line (81) leads to pressure vessel (5). In pressure vessel water (5) is evaporated and withdrawn through line (7). The resulting cooled recycle stream is recycled back to the fermentation reactor through line (6). Line (82) contains fermentation medium that is withdrawn from the process. It can be processed as desired, e.g., by providing it to a biomass separation unit, followed by further processing steps such as removal of solid fermentation product, if present, and other steps know in the art which require no further elucidation here.

Therefore, in one embodiment, the present invention pertains to a process wherein during the fermentation process a stream of the fermentation medium comprising biomass is withdrawn from the fermentation reactor, a first part of the stream is provided to the pressure vessel wherein the pressure is selected such that the temperature of the stream decreases with a value of 1-8° C. as compared to the temperature of the fermentation medium in the fermentation reactor by the evaporation of water, and recycling the thus formed stream to the fermentation reactor, and a second part of the stream is not provided to the pressure vessel.

As indicated above, the second part of the stream can be processed as desired. This embodiment is particularly attractive where the process is operated in a continuous manner.

The product of the fermentation process is a fermentation broth, which is an aqueous liquid comprising the fermentation product, biomass, and optionally further components such as impurities like are sugars, proteins, and salts.

If so desired, the fermentation broth may be subjected to a biomass removal step, e.g., a filtration step, before further processing. This is generally preferred for improving product quality. Depending on the fermentation product produced, another intermediate step may be separation of solid fermentation product, e.g., magnesium carboxylate, from the fermentation broth, before, after, or simultaneous with biomass removal, and optionally subjecting the fermentation product to a washing step.

Depending on the fermentation product produced, another intermediate step may be subjecting the fermentation broth to a concentration step to increase the concentration of fermentation product in the composition before further processing. This step may be carried out before, after, or simultaneous with biomass removal.

Other intermediate steps, e.g., purification steps, may be carried out as desired, as will be evident to the skilled person.

If the fermentation product is the salt of a carboxylic acid, a next step may be to subject the salt of the carboxylic acid to an acidification step, to convert the salt of the carboxylic acid into the carboxylic acid. In this step, the salt of the carboxylic acid is contacted with an inorganic acid to form an aqueous mixture comprising carboxylic acid and a salt resulting from the cation of the carboxylic acid salt and an anion of the inorganic acid. Examples of suitable inorganic acids include hydrochloric acid, nitric acid, sulphuric acid, and phosphoric acid.

There are various ways in which this step can be effected. The acidification step is typically conducted by bringing the carboxylate salt in contact with a solution of the inorganic acid. However, where hydrochloric acid is used, it may also be possible to contact the carboxylate salt with gaseous HCl.

The carboxylate salt may be in solid and/or dissolved form. In one embodiment, the carboxylate salt is provided in solid form. In this case, the acidification step is conducted by bringing the carboxylate salt in contact with an acidic solution. The advantage of preparing the aqueous mixture from carboxylate salt in solid form is that very high carboxylic acid concentration can thus be obtained, such as concentration of at least 15 wt. %, in particular at least 25%, up to, e.g. 50 wt. %, or e.g. 40 wt. %.

The carboxylate salt may also be in dissolved form, typically as part of an aqueous solution. In this case, the acidification step can be conducted by bringing the carboxylate salt in contact with an acidic solution or an acidic gas.

The acidification step may also be conducted on a mixture of carboxylic acid and carboxylate salt. Such a mixture may for example be obtained in a low pH fermentation. The mixture may for example be an aqueous suspension.

When acidification of the carboxylate salt is conducted by contacting it with a solution of an inorganic acid, it preferably has an acid concentration as high as possible. Such a high acid concentration will result in an aqueous mixture with a high carboxylic acid concentration, which is desirable. The acidic solution therefore comprises at least 5 wt. %, more preferably at least 10 wt. % and even more preferably at least 20 wt. % acid, based on the total weight of the acidic solution.

Acidification is typically conducted using an excess of acid. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case gaseous HCl is used, it may be contacted by bringing it in contact with a carboxylate solution or suspension. In particular, HCl gas may be blown through the solution or suspension.

Preferably, acidification is conducted at a temperature of 75° C. or less. At higher temperatures, it becomes uneconomical to adapt equipment to the harsh conditions of an acidic environment at high temperatures.

Alternatively to contacting the salt of the carboxylic acid with an inorganic acid, it is also possible to convert the salt of the carboxylic acid into the acid by contacting a solution of the salt with an ion exchange resin, for example in an ion exchange column. It is also possible to covert the salt of the carboxylic acid into the carboxylic acid using the principles of simulated moving bed chromatography, or by subjecting the solution of the salt of the carboxylic acid to electrodialysis.

The acidification step results in the formation of an aqueous liquid comprising carboxylic acid and a salt. This aqueous liquid is subjected to a separation step, optionally after intermediate processing steps have been carried out such as a concentration step.

Suitable separation steps are known in the art. The nature of the step to be used depends on the nature and properties of the acids.

Where the carboxylic acid is present in whole or in part as solid in the aqueous liquid, separation can take place using conventional solid-liquid separation methods such as filtration, centrifugation, etc.

Where the carboxylic acid is present in whole or in part as a separate organic phase in the aqueous liquid, separation can take place using conventional liquid-liquid separation methods, e.g., decantation, settling, centrifugation, use of plate separators, use of coalescers, and use of hydrocyclones.

An extractant may be added to improve the separation efficiency. Combination of different methods and apparatus may also be used.

Where the carboxylic acid is present dissolved in the aqueous liquid, separation can take place using, e.g., extraction with a suitable extractant.

Where an extractant is present in the process according to the invention, the extractant, which may also be indicated as extraction agent is substantially not miscible with water. The use of an extractant results in the formation of a two-phase system during the separation step which comprises a liquid organic layer comprising extraction agent and carboxylic acid and an aqueous layer comprising dissolved magnesium chloride chloride.

Examples of suitable extractants are aliphatic and aromatic hydrocarbons, such as alkanes and aromatic compounds, ketones, and ethers. Mixtures of various compounds may also be used.

Examples of suitable aliphatic alkanes are C5-C10 straight chain, branched, or cyclic alkanes, e.g., octane, hexane, cyclohexane, 2-ethyl-hexane, and heptane.

Examples of suitable aromatic compounds are C6-C10 aromatic compounds, e.g., toluene, xylenes, and ethylbenzene.

Examples of suitable ketones are C5+ ketones, more in particular C5-C8 ketones in the present invention. C5+ stands for ketones with at least 5 carbon atoms. The use of C9+ ketones is less preferred, The use of methyl-isobutyl-ketone (MIBK) has been found to be particularly attractive. Examples of suitable ethers are C3-C6 ethers, e.g., methyl tert-butyl ether (MTBE) and diethyl ether (DEE).

After extraction, the carboxylic acid can be separated from the extractant as desired. In one embodiment this can be done by removing the extractant by evaporation. In another embodiment the carboxylic acid can be recovered from the extractant by an extraction with water or another aqueous liquid.

After separation of the carboxylic acid from the salt, the carboxylic acid can be processed as desired. Examples of further processing steps are purification steps such as one or more of washing, active carbon treatment, recrystallization, distillation, and filtration. Where the carboxylic acid is lactic acid, it can be converted to lactide and PLA.

As will be clear to the skilled person, preferences for various aspects of the present invention can be combined, unless they are mutually exclusive.

The present invention is further illustrated by the following example, without being limited thereto or thereby.

EXAMPLE 1

A lactate fermentation was conducted in a 300 L vessel to which a 20 L pressure vessel was coupled to provide cooling to the fermentation broth. The pH was controlled using a magnesium hydroxide solution. During the fermentation a constant recirculation of 1.2 m$^3$/h was applied. The recycle stream was subjected to a vacuum pressure of 140 mbar which supplied sufficient cooling for the fermentation broth. The liquid was recirculated to the fermentation broth whereas the condensate was discarded. The temperature of the recycle stream was 2.5° C. below the temperature of the fermentation broth in the fermentation vessel. The temperature of the broth in the fermentation vessel was controlled at the desired temperature with a variation of ±0.1° C. The recycle time, defined as the time between withdrawal of a fraction of fermentation medium from the fermentation reactor and reintroduction of the fraction into the reactor, was of the order of 1 minute.

This example shows that by way of the recycle operation of the present invention with the controlled temperature of the recycle stream through the evaporation in the pressure vessel, the temperature of the broth in the fermentation vessel could controlled at the desired temperature with a variation of ±0.1° C.

The invention claimed is:

1. Process for manufacturing a fermentation product comprising the following steps:
   fermenting under fermentation conditions in an aqueous fermentation medium in a fermentation reactor with a carbohydrate source and a microorganism capable of converting the carbohydrate into a fermentation product, wherein the fermentation product is a salt or a product with a boiling point above the boiling point of water,
   during the fermentation process withdrawing part of a fermentation medium comprising the aqueous fermentation medium, fermentation product, and microbial biomass from the fermentation reactor in the form of a recycle stream,
   providing at least part of the recycle stream to a pressure vessel wherein the pressure is selected such that the temperature of the recycle stream decreases with a value of 1-8° C., as compared to the temperature of the fermentation medium in the fermentation reactor, by the evaporation of water to form a cooled recycle stream, and
   recycling the cooled recycle stream to the fermentation reactor.

2. Process according to claim 1, wherein the temperature of the recycle stream decreases with a value of 2-5° C., as compared to the temperature of the fermentation medium in the fermentation reactor.

3. Process according to claim 1, wherein the volume of the pressure vessel is between 0.1 and 10 percent of the volume of the fermentation reactor.

4. Process according to claim 1, wherein the recycle time, defined as the time between withdrawal of a fraction of fermentation medium from the fermentation reactor and reintroduction of the fraction into the reactor is at most 10 minutes.

5. Process according to claim 1, wherein solid fermentation product is present in the fermentation medium in the fermentation reactor during at least part of the fermentation.

6. Process according to claim 1, wherein the volume of fermentation medium in the fermentation reactor is at least 100 m$^3$.

7. Process according to claim 1, wherein the difference between the highest temperature of the fermentation medium in the fermentation reactor and the lowest temperature of the fermentation medium in the fermentation reactor is at most 8° C.

8. Process according to claim 1, wherein
   a first part of the recycle stream is provided to the pressure vessel, and
   a second part of the recycle stream is not provided to the pressure vessel.

9. Process according to claim 1, wherein the fermentation product is a salt of a carboxylic acid selected from the group consisting of mono-, di-, and tricarboxylic acids having 2-8 carbon atoms.

10. Process for manufacturing a fermentation product comprising the following steps:
    fermenting under fermentation conditions in an aqueous fermentation medium in a fermentation reactor with a carbohydrate source and a microorganism capable of converting the carbohydrate into an intermediate fermentation product, wherein the intermediate fermentation product is a salt of a carboxylic acid, wherein the intermediate fermentation product has a boiling point above the boiling point of water,
    during the fermentation process, withdrawing part of a fermentation medium comprising the aqueous fermentation medium and intermediate fermentation product, from the fermentation reactor in the form of a recycle stream,
    providing at least part of the recycle stream to a pressure vessel wherein the pressure is selected such that the temperature of the recycle stream decreases with a value of 1-8° C., as compared to the temperature of the fermentation medium in the fermentation reactor, by the evaporation of water to form a cooled recycle stream,
    recycling the cooled recycle stream to the fermentation reactor, and subjecting the intermediate fermentation product to an acidification step, to convert the salt of the carboxylic acid into the carboxylic acid under the formation of a aqueous mixture of a carboxylic acid and an inorganic salt.

11. Process according to claim 10, wherein the carboxylic acid is separated from the inorganic salt.

12. Process according to claim 11, wherein after separation of the carboxylic acid from the salt, the carboxylic acid is subjected to a purification step.

13. Process according to claim 12, wherein the purification step is selected from the group of consisting of washing, active carbon treatment, recrystallization, distillation, and filtration.

14. Process according to claim 10, wherein a microbial biomass removal step is carried out between the fermentation step and the acidification step.

15. Process according to claim 10, wherein the carboxylic acid is lactic acid, which is subsequently converted into lactide or polylactide.

* * * * *